(12) United States Patent
Burzynski et al.

(10) Patent No.: US 6,254,574 B1
(45) Date of Patent: Jul. 3, 2001

(54) SELF-BLUNTING NEEDLE MEDICAL DEVICES AND METHODS OF MANUFACTURE THEREOF

(75) Inventors: Mark J. Burzynski, Southbury; Alexander K. Jones, Orange, both of CT (US); Richard S. Kearns, Seattle, WA (US); John M. Polidoro; Carl R. Sahi, both of Coventry, CT (US); Chad C. Smutney, Stafford Springs, CT (US)

(73) Assignee: Bio-Plexus, Inc., Vernon, CT (US)

( * ) Notice: Subject to any disclaimer, the term of this patent is extended or adjusted under 35 U.S.C. 154(b) by 0 days.

(21) Appl. No.: 09/360,877

(22) Filed: Jul. 23, 1999

Related U.S. Application Data

(63) Continuation-in-part of application No. 08/772,002, filed on Dec. 19, 1996, now Pat. No. 5,951,520.

(51) Int. Cl.[7] .................................................. A61M 5/178
(52) U.S. Cl. ...................................... 604/170.01; 604/506
(58) Field of Search .................................... 604/158, 110, 604/159, 161, 162, 164.01, 164.07, 164.08, 164.09, 170.01

(56) References Cited

U.S. PATENT DOCUMENTS

| | | |
|---|---|---|
| 1,527,291 | 2/1925 | Zorraquin . |
| 3,491,756 | 1/1970 | Bentov . |
| 3,536,073 | 10/1970 | Farb . |
| 3,585,996 * | 6/1971 | Reynolds ................ 604/158 |
| 3,809,081 | 5/1974 | Loveless . |
| 4,068,659 * | 1/1978 | Moorehead ................ 604/159 |
| 4,121,588 | 10/1978 | Geiger . |
| 4,233,975 | 11/1980 | Yerman . |
| 4,274,408 | 6/1981 | Nimrod . |
| 4,525,157 | 6/1985 | Vaillancourt ................ 604/510 |
| 4,529,399 | 7/1985 | Groshong et al. ................ 604/510 |
| 4,613,329 | 9/1986 | Bodicky ................ 604/158 |
| 4,627,841 | 12/1986 | Dorr ................ 604/158 |
| 4,675,005 | 6/1987 | DeLuccia ................ 604/110 |
| 4,721,506 | 1/1988 | Teves ................ 604/506 |
| 4,801,295 | 1/1989 | Spencer ................ 604/198 |
| 4,808,169 | 2/1989 | Haber et al. ................ 604/195 |
| 4,810,248 | 3/1989 | Masters et al. ................ 604/192 |
| 4,828,547 * | 5/1989 | Sahi et al. ................ 604/164.06 |

(List continued on next page.)

Primary Examiner—Anhtuan T. Nguyen
(74) Attorney, Agent, or Firm—Libert & Associates; Frederick A. Spaeth

(57) ABSTRACT

A self-blunting needle medical device comprises a needle cannula (18) fixed to a hub (20) having a receiving structure therein such as ferrule (22) and a movable blunting member (14) movably received within the cannula (18). Ferrule (22) defines a passage (38) extending therethrough, within which both the cannula (18) and the movable member (14) can be received and which establishes a coaxial relationship between them. The ferrule (22) defines a first guide surface (40) for directing the blunting end (14a) of the movable member (14) into the central bore of the cannula (18) during assembly. A second guide surface (42) performs the function of guiding the mounting end (18b) of the cannula (18) into ferrule (22) for mounting therein. Typically, the cannula (18) has a tissue puncture tip (18a). When the movable member (14) is retracted into the cannula (18), the puncture tip (18a) is exposed for use, e.g., injection into tissue. The movable member (14) is then moved to an extended position in which blunting end (14a) projects beyond the puncture tip (18a), to render the device safe with regard to subsequent accidental needle sticks. Methods of assembling the self-blunting needle are also presented. In various embodiments, the guide member may be integral with the assembled device or may be defined by a guide member that is used only in the assembly process and from which the assembled device may be removed.

28 Claims, 9 Drawing Sheets

U.S. PATENT DOCUMENTS

| | | | |
|---|---|---|---|
| 4,834,718 | 5/1989 | McDonald | 604/195 |
| 4,846,805 | 7/1989 | Sitar | 604/165.04 |
| 4,869,717 | 9/1989 | Adair | 604/506 |
| 4,880,410 | 11/1989 | Rossmark | 604/110 |
| 4,911,691 * | 3/1990 | Aniuk et al. | 604/164.03 |
| 5,009,642 | 4/1991 | Sahi | 604/158 |
| 5,030,208 | 7/1991 | Novacek et al. | 604/195 |
| 5,098,389 | 3/1992 | Cappucci | 604/158 |
| 5,098,402 | 3/1992 | Davis | 604/195 |
| 5,139,485 | 8/1992 | Smith et al. | 604/158 |
| 5,201,710 | 4/1993 | Caselli | 604/110 |
| 5,205,829 | 4/1993 | Lituchy . | |
| 5,312,345 | 5/1994 | Cole | 604/110 |
| 5,334,159 | 8/1994 | Turkel | 604/158 |
| 5,376,075 | 12/1994 | Haughton et al. | 604/158 |
| 5,423,760 | 6/1995 | Yoon | 604/164.11 |
| 5,433,711 | 7/1995 | Balaban et al. | 604/192 |
| 5,460,611 | 10/1995 | Alexander | 604/110 |
| 5,470,318 | 11/1995 | Griffith, III et al. | 604/161 |
| 5,527,284 | 6/1996 | Ohnemus et al. | 604/110 |
| 5,527,291 | 6/1996 | Zadini et al. | 604/165.02 |
| 5,562,611 | 10/1996 | Transue | 604/26 |
| 5,562,629 | 10/1996 | Haughton et al. | 604/158 |
| 5,569,202 | 10/1996 | Kovalic et al. | 604/110 |
| 5,573,510 | 11/1996 | Isaacson | 604/158 |
| 5,836,916 * | 11/1998 | Corn | 604/158 |
| 5,871,470 * | 2/1999 | McWha | 604/158 |

* cited by examiner

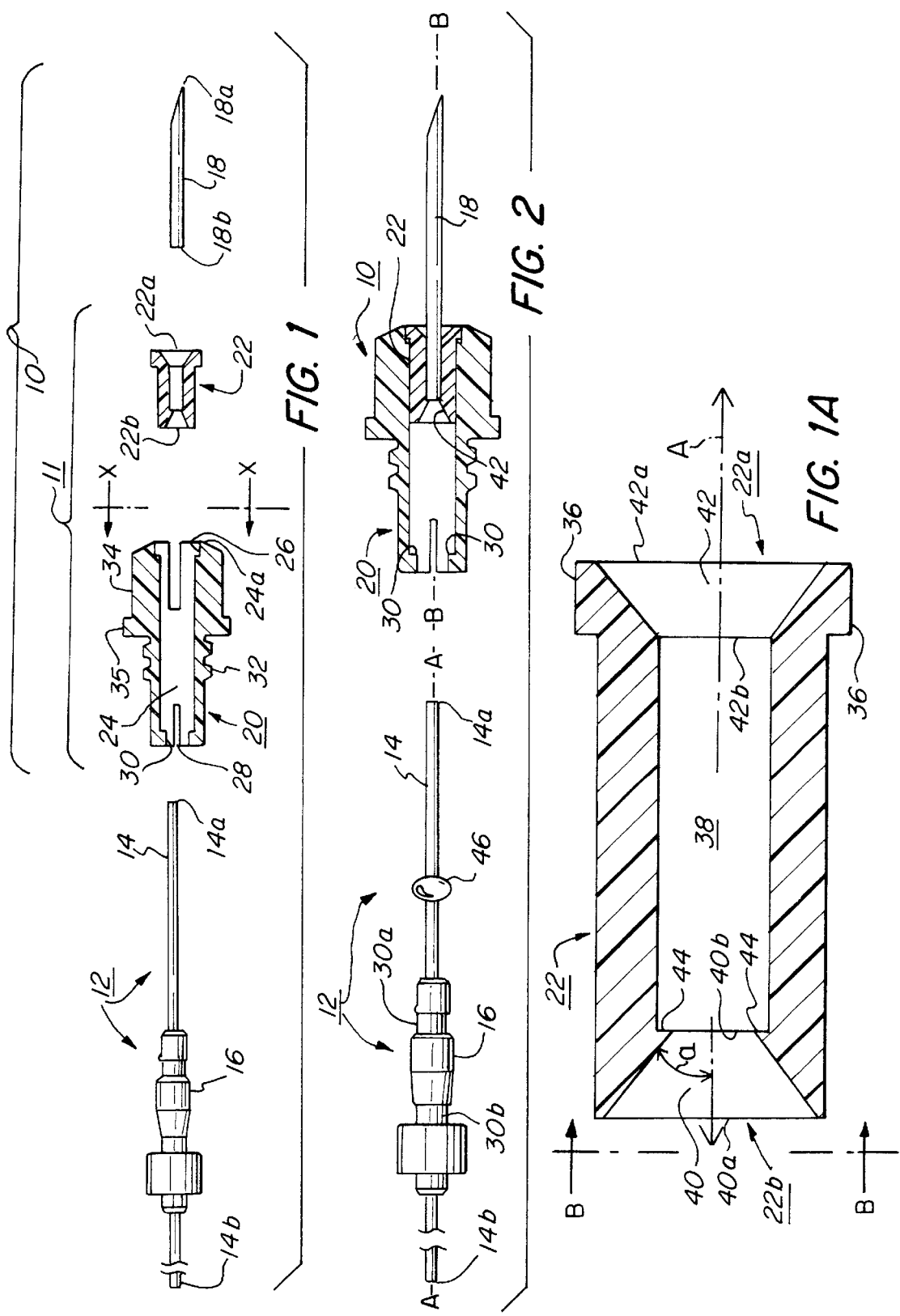

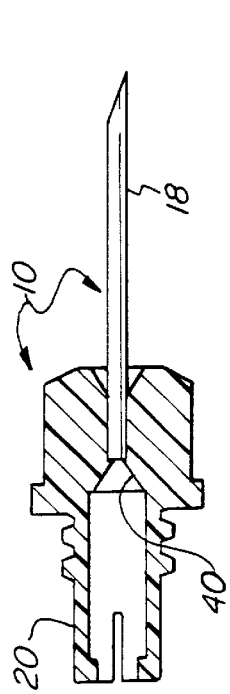
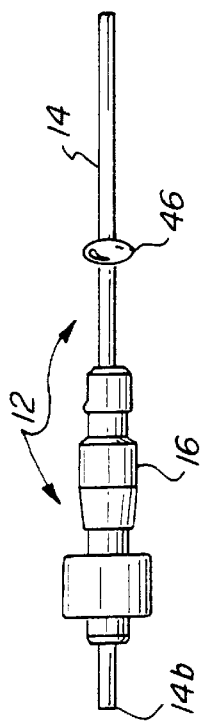
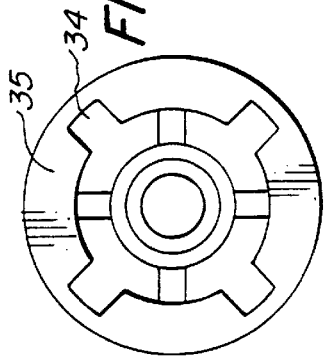
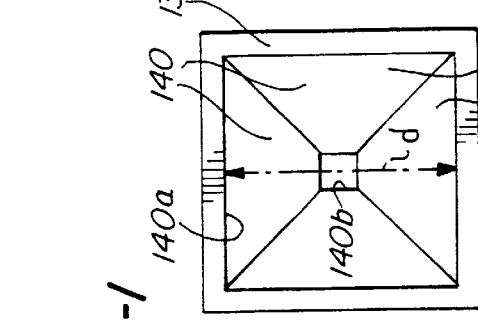
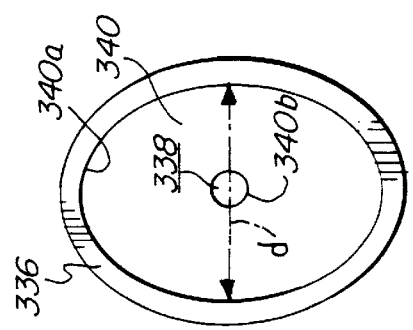
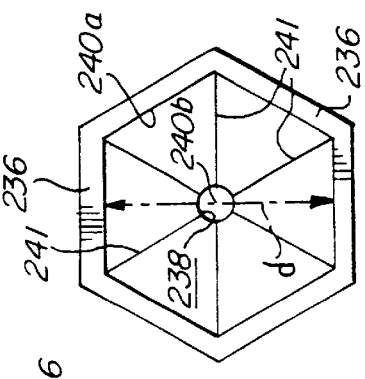
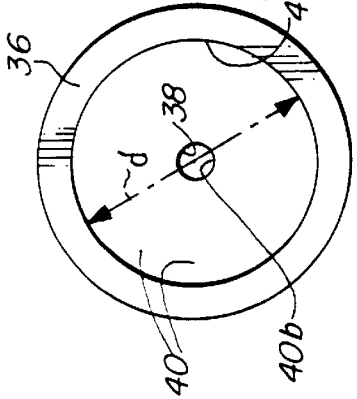

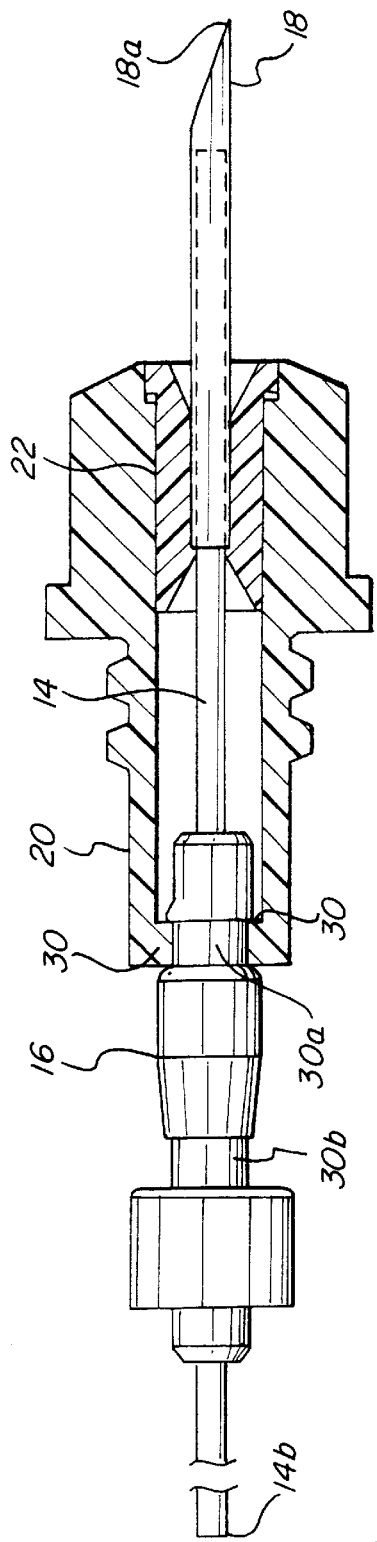
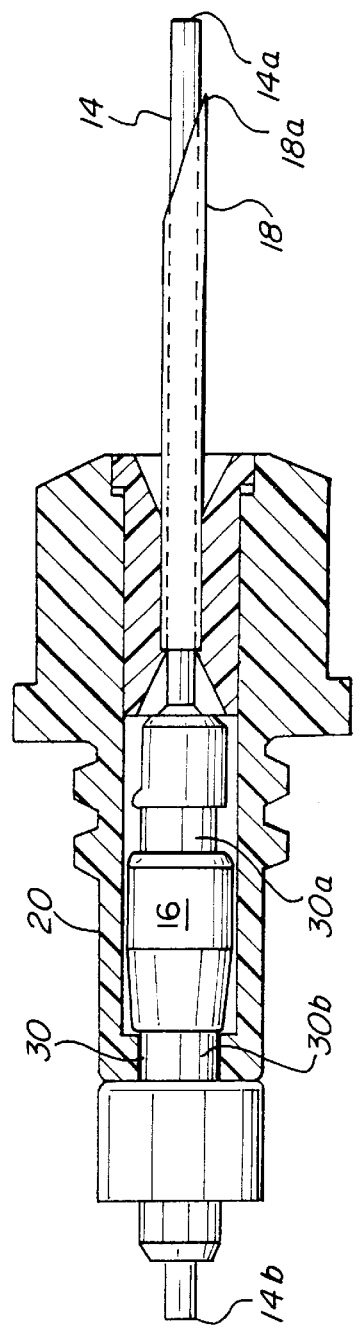
FIG. 3
FIG. 4

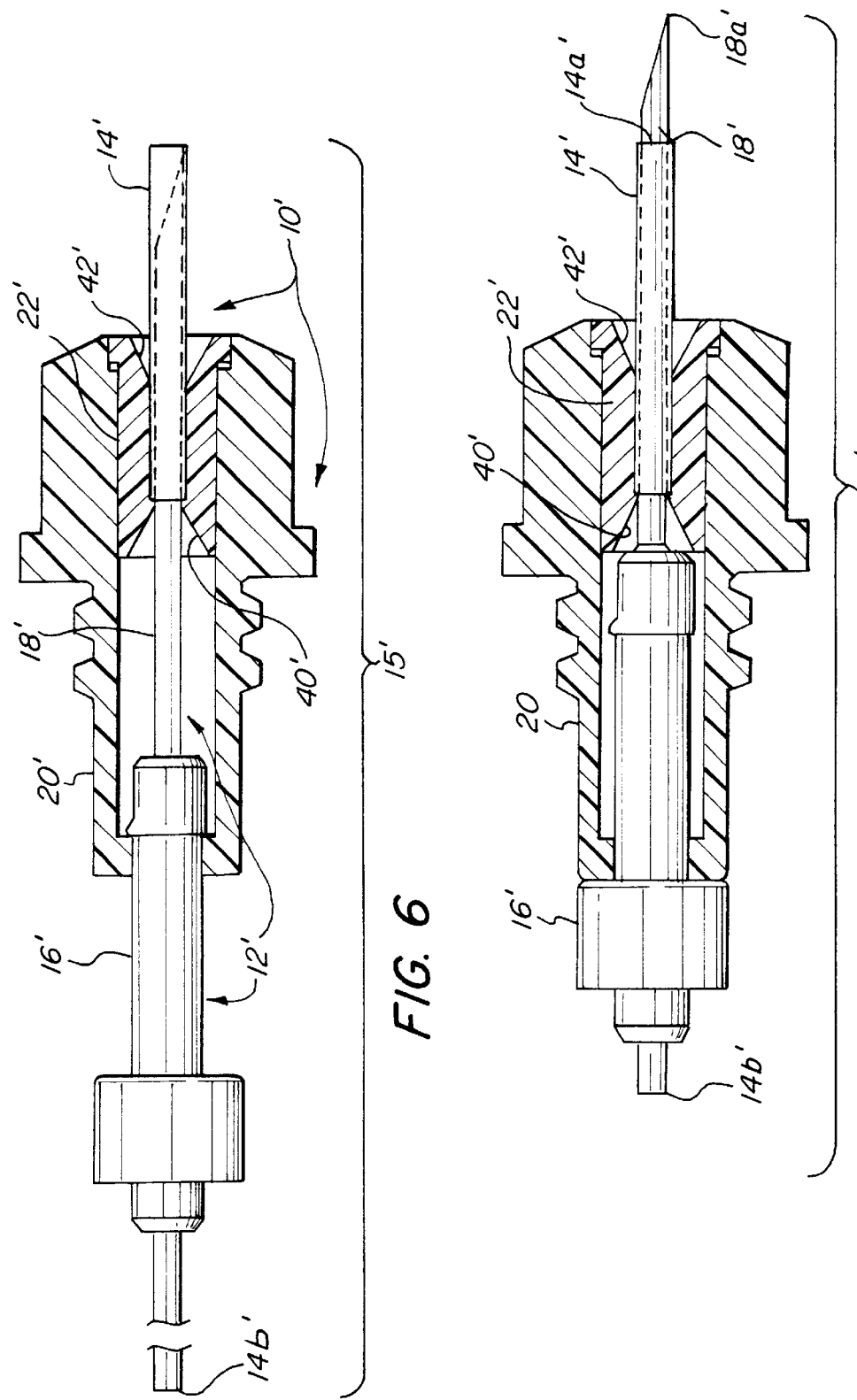

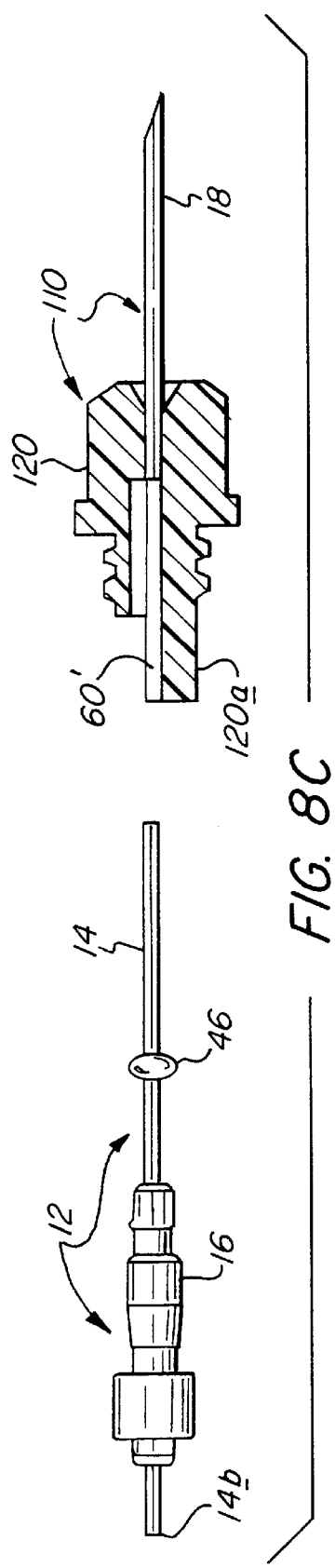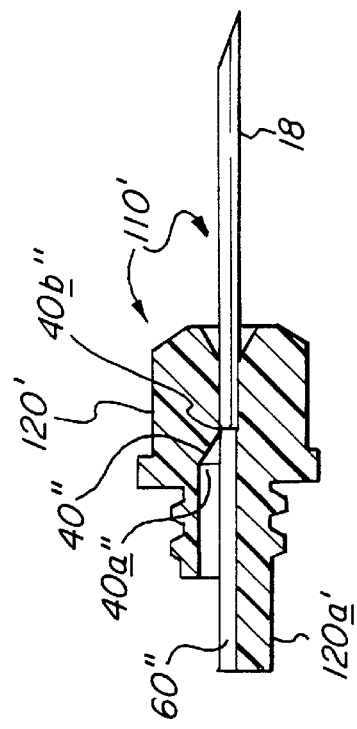
FIG. 8C
FIG. 8D

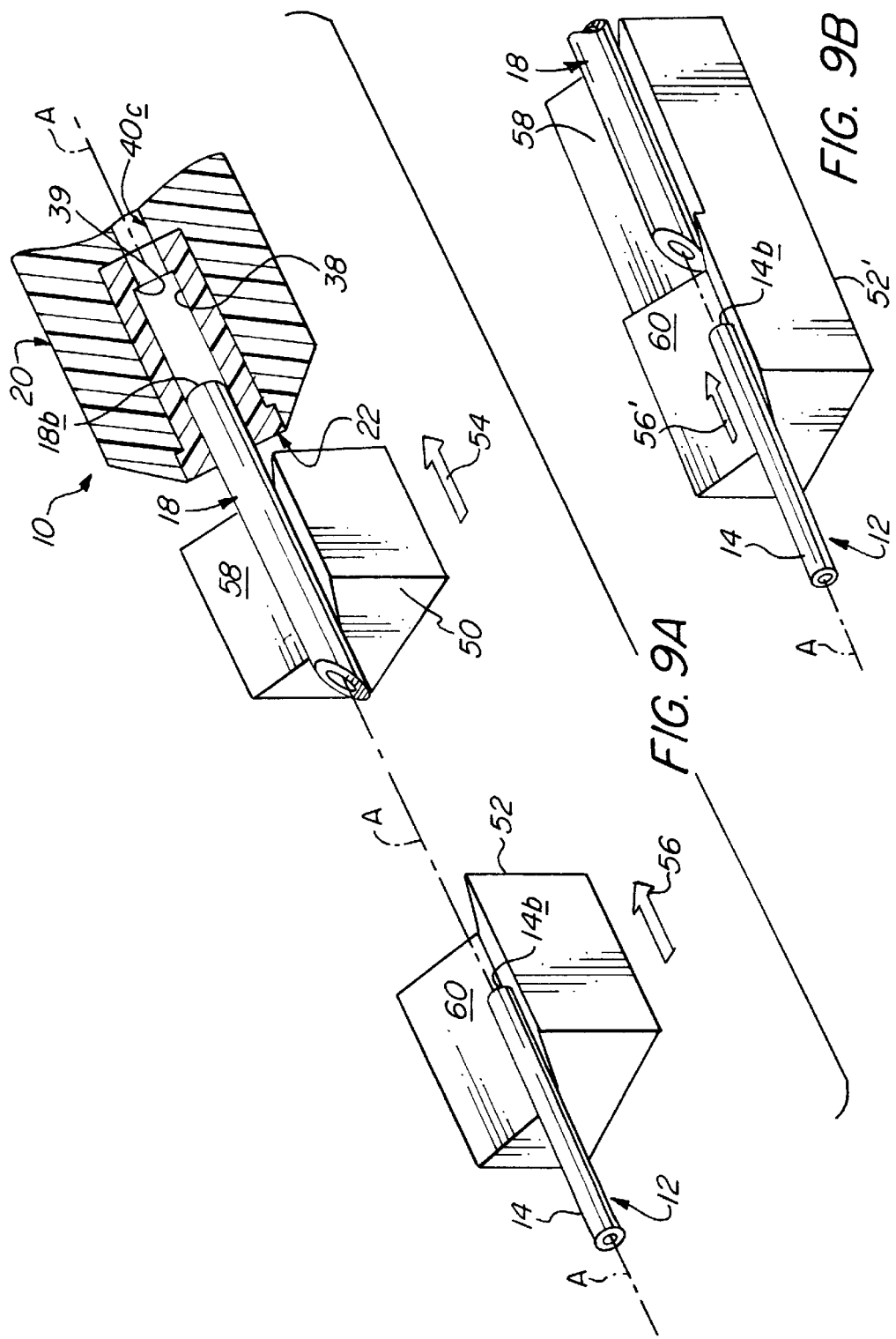

SELF-BLUNTING NEEDLE MEDICAL DEVICES AND METHODS OF MANUFACTURE THEREOF

CROSS-REFERENCE TO RELATED APPLICATION

This application is a continuation-in-part of co-pending patent application Ser. No. 08/772,002, filed Dec. 19, 1996, now U.S. Pat. No. 5,951,520 in the name of Mark J. Burzynski et al, and entitled "SELF-BLUNTING NEEDLE MEDICAL DEVICES AND METHODS OF MANUFACTURE THEREOF".

BACKGROUND OF THE INVENTION

1. Field of the Invention

The present invention relates to medical devices comprising self-blunting needles and to methods of manufacture of such self-blunting needle medical devices. More specifically, this invention is directed to improved medical devices of the type including a needle and blunting member which are movable relative to each other and to a method of manufacture thereof.

2. Related Art

For reasons which have received wide publicity, there is substantial demand for venipuncture products which may be employed by healthcare workers with minimal risk of incurring an accidental needle-stick wound. A highly successful product of this nature is a self-blunting needle assembly sold under the registered trademark "PUNCTUR-GUARD" by Bio-Plexus, Inc. of Vernon, Conn. The "PUNCTUR-GUARD" needle assembly is manufactured in accordance with the teachings of U.S. Pat. No. 4,828,547, entitled "Self-Blunting Needle Assembly and Device Including the Same", issued on May 9, 1989 to Carl R. Sahi et al. This patent is hereby incorporated by reference herein. In the "PUNCTUR-GUARD" product, a rod or probe-like blunting member is disposed within the bore of a needle cannula having a (usually beveled) puncture tip suitable for puncturing tissue. To prevent accidental needle-stick wounds from occurring after use of the device, the blunting member, which is retracted behind the puncture tip when the needle is injected into tissue, can be extended beyond the puncture tip of the needle cannula to effectively blunt the puncture tip by extending beyond it, so as to eliminate or at least greatly reduce the risk of accidental needle-stick punctures.

During production of self-blunting venipuncture products such as the "PUNCTUR-GUARD" needle assembly discussed above, the blunting member must be inserted into the back of the needle cannula. This is a process step which requires high placement accuracy. This high placement accuracy has, in the past, been achieved through the use of an adjustable position blunting member inserter which is responsive to signals provided by an optical sensor system. This process requires that the needle cannula be mounted in a hub to form a front needle sub-assembly and then positioned over a light source. If alignment conditions were perfect, light from the source would enter the beveled tip of the front needle, pass through the length of the front needle, and exit the back of the front needle as a perfect, i.e., circular, beam of light. The optical system would detect the circular beam of light, compute its position and generate control signals which would direct the blunting member inserter to bring the blunting member cannula into alignment with the front needle cannula.

Since alignment conditions are never perfect, it is difficult to detect the circular beam of light which is commensurate with precise alignment, i.e., variations within the components allow the front needle cannula to be slightly tilted within the front needle sub-assembly. The projected light beam may thus be located in an infinite number of locations. The optical system must, accordingly, locate the unique light beam for each individual front needle cannula and hub and then direct the blunting member sub-assembly inserter to this unique position for proper placement. Further, while the combination of the optical system and inserter can locate the back of the front needle cannula very accurately and then move the inserter to a position commensurate with the location, it does not precisely locate the blunting member which, of course, must enter the back of the front needle cannula for successful insertion. Thus, slight variations in the blunting member sub-assembly itself or misalignment in the clamping of the blunting member sub-assembly by the inserter can cause a failure to accurately mate the blunting member sub-assembly with the front needle sub-assembly. In summary, the step of insertion of the blunting member cannula into the back of the front needle cannula is inefficient and time-consuming.

When the above-described self-blunting needle technology is employed in a fluid collection needle, the fluid to be collected is drawn through the blunting member cannula and into an evacuated tube. Leakage of air through the space inherently existing between the blunting member outer diameter and the front needle inner diameter, such air thereafter flowing through the blunting member cannula into the collection tube, will cause undesirable foaming in the collection tube. Accordingly, in order to be suitable for use in a blood collection system, a self-blunting needle assembly must pass an air seal test. The requisite seal between the blunting member and front needle must be achieved in a manner which does not significantly impede the above briefly discussed assembly process or impede relative movement between the blunting member cannula and the needle cannula.

Therefore, there remains a need in the art for methods and apparatus which facilitate the manufacture of medical devices employing self-blunting needle technology.

Additionally, there remains a need in the art for methods and apparatus for preserving the integrity of fluid transferred through medical devices employing self-blunting needle technology by providing an improved fluid flow seal between the various components of such medical devices.

SUMMARY OF THE INVENTION

The present invention relates to a self-blunting needle cannula device comprising (a) an external component comprising a needle cannula having an outside diameter, a through-bore having a through-bore diameter, a tip comprising a puncture tip, a mounting end, and an external component hub on the needle cannula spaced from the tip, and (b) an internal component comprising an elongate blunting member having a tip defining a blunt tip, and an internal component hub on the blunting member and spaced from the tip, the blunting member being disposed within the through-bore of the needle cannula. The external component and the internal component are movable relative to each other between a sharpened configuration, in which the blunt tip is positioned short of the puncture tip of the needle cannula to leave the puncture tip exposed, and a blunting configuration, in which the blunt tip extends beyond the puncture tip of the needle cannula to effectively blunt the device. There is also a guide surface on the device that leads axially towards the through-bore so that the guide surface can serve as a guide for the insertion of the blunting member into the through-bore during assembly of the device.

According to one aspect of the invention, the guide surface may converge axially from a first entry aperture larger than the through-bore to a first gate aperture not larger than the through-bore, the first gate aperture being aligned with the through-bore.

According to another aspect of the invention, the guide surface may comprise a non-convergent surface that defines a groove that is positioned and configured to guide the blunting member into the through-bore of the needle cannula.

According to another aspect of the invention, a guide surface may define a first entry aperture which may optionally have a diameter in the range of from about 0.5 to 0.009 inch and a first gate aperture which may optionally have a diameter in the range of from about 0.203 to 0.006 inch.

According to still another optional aspect of the invention, the needle cannula may define a longitudinal axis and wherein the guide surface may define an angle α relative to the needle cannula axis, the angle optionally having a magnitude in the range of from about 5 to 75 degrees.

In specific embodiments of the present invention, a self-blunting needle cannula device may comprise a guide member disposed at the mounting end of the needle cannula, the guide member defining the guide surface. The guide member may be disposed within the external component hub or it may be integrally formed as part of the external component hub. In a particular embodiment, the guide member may comprise an alignment lug formed on the external component hub. The guide member may have a first end at which the guide surface is formed and an opposite, second end at which is optionally formed a second entry aperture larger than the needle cannula and a second guide surface that converges axially to a second gate aperture smaller than the second entry aperture but not smaller than the needle cannula. There may be a passage extending between and axially aligned with the first and second gate apertures, the needle cannula extending through the second gate aperture and the mounting end of the needle cannula being mounted within the passage, and the second guide surface may converge from the second entry aperture towards the bore to the second gate aperture, to serve as a guide for the insertion of the mounting end of the needle cannula into the passage during assembly of the device. Optionally, the first gate aperture may be smaller than the passage in the guide member and smaller than the needle cannula so that the guide member defines in the passage a stop shoulder at the first gate aperture.

Optionally, like the first guide surface, the second entry aperture may have a diameter in the range of from about 0.5 to 0.009 inch and the second gate aperture may have a diameter in the range of from about 0.203 to 0.006 inch. The second guide surface may optionally define an angle α relative to the needle cannula axis having a magnitude in the range of from about 5 to 75 degrees.

A needle device as described above may be combined with a syringe comprising an actuation member for moving the device from a sharpened configuration to a blunted configuration.

The present invention also provides a self-blunting needle cannula device comprising (a) an external component comprising a blunting member having an outside diameter, a through-bore having a through-bore inside diameter, an outward end comprising a blunt tip, a mounting end, and an external component hub on the blunting member and spaced from the tip, and (b) an internal component comprising an elongate needle cannula having an outward end comprising a puncture tip, and an internal component hub on the needle cannula and spaced from the puncture tip, the needle cannula being disposed within the through-bore of the blunting member of the external component. The external component and the internal component are movable relative to each other between a sharpened configuration in which the blunt tip is positioned short of the puncture tip of the needle to leave the puncture tip exposed and a blunted configuration in which the blunt tip extends beyond the puncture tip of the needle to effectively blunt the device. There is a guide surface on the device that leads axially towards the through-bore to serve as a guide for the insertion of the needle cannula into the through-bore during assembly of the needle cannula device. The guide surface may optionally be defined by a guide member both of which may be configured as described above.

The present invention also relates to a method for assembling a device comprising inserting an internal component within an external component having an axially-extended through-bore therein dimensioned and configured to receive the internal component and provides an improvement comprising advancing the internal component into contact with a guide surface configured to lead axially to the through-bore to guide the internal component into the bore to produce an assembled device. The method may comprise advancing the internal component into contact with a non-convergent guide surface or into contact with an axially convergent guide surface. The axially convergent guide surface may be configured as described above.

Optionally, the method may include contacting the external component with a first guide surface and contacting the internal component with a second guide surface.

In a particular embodiment, the guide surface is provided by a non-integral guide member and the method comprises removing the assembled device from the guide member. Optionally, the method may include passing the internal component through the guide member and removing the assembled device from the guide member. The method may also comprise securing a nut to the internal component after the internal component passes through the guide member.

A method according to this invention may comprise (a) positioning a guide member having a guide surface relative to the external component so that the guide surface leads axially to the through-bore, and (b) advancing the blunting member into contact with the guide surface to guide the blunting member into the through-bore of the needle cannula. Optionally, the method may comprise disposing the needle cannula on a first guide surface and advancing the blunting member into contact with a second guide surface.

Alternatively, the method may comprise providing a guide member having a first end and a second end and a passage that extends axially from the first end to the second end and further comprising at the first end a first guide surface that leads axially to the passage and at the second end a second guide surface that leads axially to the passage, wherein the passage is sized to receive the needle cannula. The method may then comprise disposing the needle cannula with its mounting end disposed towards and in alignment with the second guide surface and advancing the needle cannula into contact with the second guide surface and into the passage and into alignment with the first gate aperture.

Optionally, the method may include installing the self-blunting needle device in a medical fluid-handling device comprising an actuation member for moving the device between the sharpened configuration and the blunted configuration.

The method described above may be used analogously to assemble a self-blunting needle device comprised of (i) an external component comprising a blunting member having an outside diameter, a through-bore having a bore inside diameter, an outward end comprising a blunt tip and a mounting end; and (ii) an internal component comprising an elongate needle cannula having an outside diameter and an outward end comprising a puncture tip, and, after assembly, being disposed within the through-bore of the cannula member of the external component.

Other aspects of the present invention are described below.

BRIEF DESCRIPTION OF THE DRAWINGS

In the accompanying drawings, like reference numerals refer to like elements in the several Figures.

FIG. 1 is an exploded elevation view, partly in cross section, of a self-blunting needle device in accordance with one embodiment of the present invention in which the blunting member is disposed within the needle cannula;

FIG. 1A is an enlarged view of the ferrule 22 of FIG. 1 in which the diameter of passage 38 is arbitrarily enlarged relative to the diameter of the ferrule 22 for clarity of illustration;

FIG. 1A-1 is an end view taken along line X—X of FIG. 1;

FIG. 1B is an end view, taken along line B—B of FIG. 1A, but with the diameter of passage 38 reduced in size relative to that shown in FIG. 1A;

FIG. 1C is a view similar to FIG. 1B of another embodiment of the ferrule;

FIG. 1D is a view similar to FIG. 1B, but of a third embodiment of the ferrule;

FIG. 1E is a view similar to FIG. 1B, but of a fourth embodiment of the ferrule;

FIG. 2 is a view similar to that of FIG. 1 but showing the device in an assembled state with the body and viscous lubricant applied to the blunting member cannula;

FIG. 2A is a view similar to that of FIG. 2 of an alternative embodiment of the invention;

FIG. 3 is an elevation view, partly in cross section, of the needle device of FIGS. 1 and 2 in the ready-to-use condition showing the blunting member in the retracted position;

FIG. 4 is a view, similar to that of FIG. 3, showing the blunting member in the extended position;

FIG. 5 is a side elevation view, partly in cross section, of a needle device in which the cannula is disposed within the blunting member in accordance with an alternative embodiment of the invention, showing the device in a sharpened configuration;

FIG. 6 is a view, similar to FIG. 5, showing the device in a blunted configuration;

FIG. 8C is a partially cross-sectional view of a blunting member aligned for insertion into a needle member comprising a guide member in accordance with the present invention;

FIG. 8D is a cross-sectional view of a needle member according to an alternative embodiment of the invention;

FIG. 9A is a schematic perspective, partly cross-sectional view of a guide member for assembly of the needle cannula, blunting member and external hub (shown in cross section) in accordance with an embodiment of the present invention;

FIG. 9B is a schematic perspective view of a guide member for use in an alternative embodiment of the invention;

DETAILED DESCRIPTION OF THE INVENTION AND PREFERRED EMBODIMENTS THEREOF

Figure 8A:
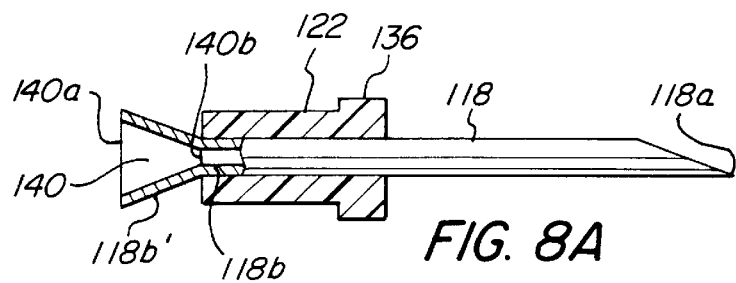
FIG. 8A is a side view in elevation, partly broken away, of an external component comprising a cannula member usable in a needle device similar to that illustrated in FIG. 1.

The present invention relates to self-blunting needle assemblies of the type that comprise a needle cannula and a blunting member disposed telescopically one within the other, one comprising an external component having a through-bore there-through and the other comprising an internal component that is received within the through-bore. The blunting member may be disposed within the needle cannula or, in alternative embodiments, the blunting member may be hollow and the needle cannula may be disposed within the blunting member. In either case, the blunting member and the needle cannula are movable relative to each other between a sharpened configuration and a blunted configuration, i.e., from the sharpened configuration to the blunted configuration or from the blunted configuration to the sharpened configuration and, optionally, back again. In the sharpened configuration (optionally also referred to as the "insertion configuration"), the puncture tip of the needle cannula extends beyond the tip of the blunting member so that the puncture tip is unimpeded upon being inserted into tissue. In the blunted configuration, the blunting member extends beyond the puncture tip of the needle cannula and thus effectively blunts it, thereby preventing, or at least severely inhibiting, the puncture tip from entering tissue. One aspect of the present invention provides an improvement to such assemblies that simplifies the insertion of one of the needle cannula and the blunting member into the other and, accordingly, provides a simplified assembly procedure.

Another aspect of the present invention pertains to the assembly having a guide surface that leads axially to the through-bore so that the internal component can be brought to bear on the guide surface and advanced in an axial direction, optionally while in contact with the guide surface, into the through-bore of the external component. As used herein and in the claims, the term "lead axially" to the through-bore means that the guide surface extends in an axial direction and does not include or lead to a perpendicular shoulder or other catch surface at the entrance of the through-bore that would inhibit an axially-moving internal component that is sliding along the surface to the through-bore from entering the through-bore. A perpendicular shoulder provides a surface that is disposed perpendicularly, i.e., radially and without axial aspect relative to the through-bore axis.

In a particular embodiment, the guide surface may have a funnel-like configuration and may define an entry aperture and an exit aperture or gate aperture. The entry aperture is larger than the through-bore of the external component (e.g., the through-bore of a needle cannula or blunting member) and the exit aperture or gate aperture is not larger than the through-bore. For ease of expression, the terms "larger" and "smaller" are sometimes used herein and in the claims as a shorthand to indicate the relative sizes of the structures whose sizes might be stated in terms of their smallest diameters, as would be convenient for structures configured to have circular or otherwise radially symmetric cross-sectional configurations. In addition, these terms also indicate that the periphery of one structure or aperture can be positioned within the periphery of another, regardless of their geometric configurations. In such an embodiment, the guide surface leads axially to the through-bore by converging from the entry aperture to an exit aperture or gate aperture of comparatively smaller radius, i.e., the guide surface converges axially to the gate aperture and, by having the gate aperture aligned with the through-bore, thus converges axially to the through-bore. When used in connection with such embodiment, the term "gate aperture" refers to the portion of the guide surface at which the guide surface stops converging. In addition, the term "converge axially" means that the guide surface has no shoulder perpendicular to the through-bore axis or other catch surface adjacent the gate aperture or exit aperture. The guide surface may be defined by a surface of a guide member that constitutes an integral part of the needle device. For example, the guide member may be in the form of part of a hub secured onto the end of the external component, or of a distinct ferrule secured at the end of the external cannula, or in the form of part of the external component cannula itself. Alternatively, the guide member may comprise a structure that is not integral to the assembled needle device (or other assembled internal component/external component assembly), i.e., it may comprise a structure from which the assembled device may be removed. In such case, the guide member may be re-used to facilitate the production of multiple devices, as described below.

With reference to FIGS. 1 and 2, a self-blunting needle cannula device in accordance with one embodiment of the present invention comprises an external component indicated generally at 10, and including a hub-ferrule subassembly 11, and an internal component indicated generally at 12. The external component 10 is depicted in an exploded state and is seen to comprise a cannula member in the form of a needle cannula 18, an external component hub 20 and a ferrule 22. As will be clear by reference to FIG. 2, hub 20 is mounted on needle cannula 18 by means of the ferrule 22. Needle cannula 18 has a tip that comprises a puncture tip 18a for penetrating biological tissue, sealing membranes for specimen containers and the like, and an opposite, mounting end 18b that may be blunt. Needle cannula 18 has a central bore extending therethrough from the puncture tip 18a to the mounting end 18b to permit the passage of fluid therethrough and, as explained below, to movably accommodate the blunting member of the internal component 12 therein. Hub 20 is preferably a generally tubular member, i.e., has a longitudinal hub bore 24 extending therethrough. Hub bore 24 is enlarged at the end of the hub from which needle cannula 18 extends to define a shoulder 26. Hub 20 is split at its end opposite from shoulder 26 so as to impart a degree of flexibility to that end. This split in hub 20 is formed by a pair of opposed slots 28. A pair of detents 30, which project into bore 24, are provided in the split end of hub 20. The detents 30 cooperate, in the manner shown in FIGS. 3 and 4, with recesses provided on the exterior of the internal component hub 16 of internal component 12 to hold blunting member 14 in particular positions relative to needle cannula 18, as further described below. In this illustrated embodiment, hub 20 is provided with an exterior thread 32 whereby the external component 10 may be engaged with a threaded needle holder of a fluid-handling device such as a syringe (not shown). As best seen in FIG. 1, the hub 20 is also provided with a plurality of external fins 34, oriented generally radially with respect to the axis of bore 24, which external fins extend from a circumferential flange 35 at the end of thread 32 to the end of hub 20 where the shoulder 26 is located. The external fins 34 facilitate handling of the hub 20 to install or remove external component 10 into or out of a holder or other device (not shown).

As best shown in FIG. 1A, the ferrule 22 has a first end 22a and a second end 22b and is sized and shaped to be inserted, as a press fit, into the first end 24a of hub bore 24 of hub 20. Referring to FIGS. 1A and 1B, ferrule 22 has a circumferential ferrule flange 36, which is complementary in shape to the recess which defines shoulder 26 (FIG. 1) of external component hub 20. Ferrule 22 may optionally be glued in place within hub 20. Ferrule 22 is a substantially tubular member and defines a passage 38 that diverges at the two opposite ends thereof where the ferrule 22 defines conical lead-ins, i.e., a first guide surface 40 and a second guide surface 42. Guide surface 40 defines a first entry aperture 40a and a first gate aperture 40b disposed at the first end of passage 38. First entry aperture 40a is of larger diameter than the diameter of first gate aperture 40b so that ferrule 22 defines, in part, a conical or funnel-like configuration. Optionally but preferably, the diameter of first entry aperture 40a exceeds the diameter of the first gate aperture by at least about 0.01 inch. Guide surface 40 defines an acute angle α relative to the longitudinal axis A of passage 38. The magnitude of angle α will typically, but not necessarily, be at least about 5 degrees, optionally at least about 7.5 degrees, or at least about 10 degrees (which correspond to included angles of at least about 10, 15 or 20 degrees, respectively) and will typically but not necessarily be not more than about 75 degrees, e.g., not more than about 70 degrees or optionally not more than about 65 degrees. Thus, angle α may be in the range of from about 5 to 75 degrees, e.g., about 7.5 to 70 degrees, about 5 to 70 degrees, etc. In a particular embodiment, angle α may be, e.g., about 45 degrees. The diameter of first gate aperture 40b is not larger than the diameter of passage 38 and preferably not larger than the diameter of the through-bore of the needle cannula to be inserted into passage 38. The first entry aperture is sized to readily permit insertion therein of a cannula or rod-like member and alignment thereof with guide surface 40 during assembly of the self-blunting needle cannula device without need to resort to optical alignment equipment or other extraordinary measures. Needle cannula stock used in medical devices typically ranges in outside diameter from about 0.203 inch (gage 6RW) to about 0.006 inch (gage 34RW). A typical useful range of diameter for first entry aperture 40a (and for second entry aperture 42a) for such a range of needle cannula stock is from about 0.5 to 0.009 inch. The associated gate aperture will be sized either to be not larger than the through-bore of the needle cannula (in the case of a first gate aperture) or not smaller than the needle cannula (in the case of a second gate aperture), but in either case a suitable size for the associated gate aperture may be in the range of from about 0.203 to about 0.006 inch.

Reference to the diameters of the entry apertures 40a, 42a, and the gate apertures 40b, 42b, and the truncated right-angle conical construction of first guide surface 40 and second guide surface 42, should not be taken to mean such circular/conical construction is essential to the present invention. For example, FIGS. 1C, 1D and 1E illustrate alternate embodiments of non-circular construction of first entry and gate apertures and non-conical construction of the first guide surface. FIG. 1C shows a first guide surface 140 comprised of four trapezoidal-shaped flat surfaces extending between a first entry aperture 140a and a first gate aperture 140b, both apertures being square in cross-section in the illustrated embodiment. First gate aperture 140b leads to passage 138. Obviously, a rectangular configuration other than a square may be used, e.g., any suitable polygonal configuration may be used. The circumferential ferrule flange 136 of the FIG. 1C embodiment is also shown as square in cross-sectional view but, alternatively, circumferential ferrule flange 136 could be circular in cross-section, with the remainder of the construction being as shown in FIG. 1C.

FIG. 1D illustrates another embodiment in which first entry aperture 240a and circumferential ferrule flange 236 are of hexagonal configuration, and first gate aperture 240b is of circular configuration. In this embodiment, the trapezoidal-shaped surfaces connecting the hexagonal first entry aperture 240a to first gate aperture 240b may be flat, or they may be curved surfaces defining valleys which meet at crests which lie along the lines 241. First gate aperture 240b leads to passage 238.

FIG. 1E shows yet another embodiment of which the first entry aperture 340a is oval in cross-sectional view, and the first gate aperture 340b is circular. The latter leads to passage 338. In this case the first guide surface 340 is a smooth, curved surface and circumferential ferrule flange 336 is of oval configuration in cross-sectional view.

Other variations of the construction of the first (and second) guide surface may be utilized, such as polygonal configurations other than a square, rectangle or hexagon, and even irregularly shaped first (and second) entry and gate apertures may be used if necessary to accommodate a particular construction. In all cases, reference herein and in the claims to the "diameter" of the entry and gate apertures refers to the smallest diameter thereof as illustrated in each of FIGS. 1B through 1E by the diameter lines d.

Returning now to the description of the ferrule 22, first gate aperture 40b thereof is slightly smaller in diameter than passage 38 and, accordingly, provides an annular stop shoulder 44 at the junction of first guide surface 40 and the adjacent portion (first end) of passage 38. At the opposite end of ferrule 22, an optional second guide surface 42 extends between a second entry aperture 42a and a second gate aperture 42b. The first gate aperture 40b is slightly smaller in diameter than the second gate aperture 42b, which is the same diameter as passage 38. The outer diameter of needle cannula 18 is about the same as, or only very slightly less than, the diameter of passage 38.

External component 10 is assembled by inserting the second end 22b of ferrule 22 into the first end 24a of the bore 24 in hub 20 until ferrule flange 36 engages shoulder 26. Then, the mounting end 18b of needle cannula 18 is disposed towards and aligned with second entry aperture 42a and second guide surface 42. The mounting end 18b is then advanced into contact with guide surface 42 and, optionally, while in contact with guide surface 42, is further advanced towards passage 38 for insertion through second gate aperture 42b and into passage 38 of ferrule 22, preferably until mounting end 18b seats against stop shoulder 44, thus producing an assembled external component 10 as shown in FIG. 2. The insertion of the mounting end 18b into ferrule 22 is facilitated by the guiding action of the second guide surface 42, second entry aperture 42a providing a larger "target" for insertion of needle cannula 18b and the truncated conical shape of second guide surface 42 guiding mounting end 18b into passage 38. Optionally, needle cannula 18 may be glued in place in ferrule 22, e.g., by an ultraviolet ("UV")-curable adhesive, as is known in the art.

The internal component 12 may be assembled in a conventional manner, e.g., by inserting the blunting member 14 through the internal component hub 16 and securing the hub 16 in place thereon, e.g., by the use of a UV-curable adhesive. The first end of blunting member 14 is provided by a blunt end 14a which, under ordinary hand pressure, will not easily puncture human skin or other biological tissue. The opposite end 14b of blunting member 14 extends beyond internal component hub 16, in the direction facing opposite to blunt end 14a.

To prepare for the assembly of a self-blunting cannula device, internal component 12 is disposed either manually or by the use of a conventional piece handling device so that the longitudinal axis A—A (FIG. 2) of internal component 12 is in approximately parallel relation to the longitudinal axis B—B (FIG. 2) of external component 10, which is set in position either manually or by another conventional piece handling device. The blunt end 14a of blunting member 14 is disposed towards and aligned with the first entry aperture 40a and first guide surface 40 of ferrule 22. Then, internal component 12 is advanced towards external component 10 until the first end 14a of blunting member 14 passes through first entry aperture 40a and contacts first guide surface 40 which, with continued advancement of internal component 12, guides the blunt end 14a of blunting member 14 through first gate aperture 14b thence into the bore of needle cannula 18. As with the insertion of mounting end 18b of cannula needle 18 into ferrule 22, the first entry aperture 40a provides a larger target than passage 38 or the bore of needle cannula 18, and the truncated conical shape of first guide surface 40 guides blunting member 14 into place. The present invention compensates for misalignment of the blunting member with the needle through-bore because the guide surface converges axially from an aperture larger than the through-bore to an aperture that is not larger than the through-bore and that is aligned there-with, so the guide surface would guide the tip of the blunting member into the through-bore as discussed herein. The self-blunting cannula device can then be disposed in the ready-to-use configuration illustrated in FIG. 3. It is thus readily seen that providing a first guide surface 40 eliminates the need to precisely align the internal component 12 with the bore of the external component needle cannula 18. In contrast, prior art U.S. Pat. No. 4,828,547 shows in FIG. 1A a needle mouth (16) that does not lead or converge axially to a gate aperture or exit aperture not larger than the through-bore of the needle because there the floor (16c) is disposed solely radially, i.e., perpendicularly, relative to the axis of the needle cannula and the bore (34) herein. The floor (16c) is formed because the interior surface of the needle mouth 16) axially converges only to a diameter greater than that of the through-bore, i.e., to the outside diameter of floor (16c). If, while attempting to insert the blunting member or "probe" (40) into the needle bore, the probe is out of alignment with the bore, it will bear against the floor (16c) and will get caught there because the floor (16c) is perpendicular to the through-bore axis and so is not configured to guide the probe into the bore. For this reason the prior art made use of elaborate optical positioning or other such equipment that may be dispensed with by the practice of the present invention.

Preferably, the first gate aperture 40b is not larger in diameter than the passage 38 at least at the first end thereof, so that the formation of a lip or shoulder facing first entry aperture 40a is precluded, as such lip or shoulder could inhibit entry of the blunting member 14 therein. Optionally, first guide surface 40 may be formed as an integral part of hub 20, as indicated in FIG. 1A. In any case, by providing a first guide surface 40 that preferably defines a first gate aperture 40b that is no larger than the interior of needle cannula 18, the insertion of internal component 12 into external component 10 is simplified. Generally, first guide surface 40 (like second guide surface 42) preferably is shaped like a truncated right-angle cone.

The internal component 12 and the external component 10 can be prepared separately and, optionally, simultaneously. In such production, where adhesive bonding is employed, a UV-curable adhesive will optimally be utilized. The internal component 12 may be fabricated by dropping the blunting member 14 into the internal component hub 16 and adhesively bonding the parts. The external component 10 may be fabricated by first pressing the ferrule 22 into the hub 20. Then, the mounting end 18b of needle cannula 18 is guided, by means of the second guide surface 42, into ferrule 22 until end 18b seats upon shoulder 44. Second guide surface 42 extends between second entry aperture 42a and second gate aperture 42b and is, like first guide surface 40, shaped like a segment of a right-angle cone. Optionally, needle cannula 18 may be gravity-fed into ferrule 22. When needle cannula 18 is in place in ferrule 22, it may be adhesively secured therein.

To complete the assembly, the internal component 12 is disposed with its longitudinal axis A—A (FIG. 2) generally parallel to the longitudinal axis B—B of the external component 10, with the first end of the internal component 12 in alignment with the first entry aperture 40a (FIG. 1A) of first guide surface 40, to facilitate insertion of the internal component 12 into the external component 10. Reference to the end of the internal component 12 being in alignment with the first entry aperture 40a means that when the internal component 12 and the external component 10 are brought together in a direction substantially parallel with their respective longitudinal axes, the end of the blunting member 14 will pass through first entry aperture 40a to contact the first guide surface 40. When the internal component 12 is so disposed, it is advanced towards the first gate aperture 40b of first guide surface 40. Ultimately, the blunt end 14a of the blunting member 14 contacts the first guide surface 40 and, as the internal component is advanced further, the funnel-like or conical configuration of first guide surface 40 will lead the end of blunting member 14 to the first gate aperture 40b (FIG. 1A) which is aligned with and disposed at the mounting end 18b (FIG. 1) of the bore of needle cannula 18. Since the first gate aperture 40b is no larger than the interior bore of needle cannula 18, first guide surface 40 will readily guide blunting member 14 into the central bore of needle cannula 18 without "hanging up" or catching at first gate aperture 40b. (It is to be understood that reference to one member being "advanced" toward another, or terms of similar import, are relative terms and that such phrases apply equally to procedures in which the internal component is held stationary while the external cannula component is moved "backward" towards it, or both are moved towards each other.) It is thus seen that ferrule 22 serves as a guide member that becomes integral with the assembled device in accordance with one embodiment of the present invention. (In other embodiments as described below, the guide member is a tool or fixture which does not become part of the assembled device.) In the illustrated embodiment, the completed self-blunting needle assembly 15 (FIG. 3) is ready for use when the blunting member 14 is held in the retracted position shown in FIG. 3, as described more fully below.

Preferably, the external diameter of blunting member 14 is a close fit with the internal diameter of needle cannula 18 so that the puncture tip 18a lies flat on the surface of the blunting member when the blunting member is in its extended position, shown in FIG. 4. To allow fluid flow through the cannula, it is therefore necessary in this preferred embodiment that the blunting member be hollow and that it have a central bore extending therethrough. In alternate embodiments, however, an internal blunting member need not be hollow to accommodate fluid flow therethrough, but in such case the blunting member must have a diameter sufficiently smaller than the internal diameter of the needle cannula to allow adequate fluid flow in the annular space between them.

When the internal component is dimensioned and configured for a close fit with the interior bore of the external component, it may be desirable to lubricate their mating surfaces and to provide a seal between them to prevent the flow of air or other fluids between those surfaces. Accordingly, in the illustrated embodiment of FIGS. 1–3, a drop of viscous sealant-lubricant, indicated at 46 in FIG. 2, is applied to the blunting member 14. Because of its viscosity, the lubricant will assume the shape of an annulus, i.e., the lubricant will extend completely about the blunting member cannula 14. In the practice of the present invention, satisfactory results have been achieved by employing a thickened lubricant having a viscosity which is comparable to that of petroleum jelly, such as a high viscosity silicone (i.e., organo-silicon polymer)-based lubricant. After the viscous lubricant 46 has been applied, the internal component 12 is advanced into hub 20. This relative motion will result in the projecting detents 30 at the split end of hub 20 snapping into the first annular groove 30a formed in the exterior of the internal component hub 16 of the internal component 12. At this juncture, the self-blunting needle assembly 15 will be in the state depicted in FIG. 3, in which the self-blunting needle assembly 15 is ready to be incorporated into a medical device such as a syringe. At this time, the viscous lubricant 46 will be located in the annular or cylindrical space between the outer surface of the blunting member 14 and the inner surface of the needle cannula 18. The viscosity of the lubricant 46 ensures that a good seal will be established between the tubular blunting member 14 and needle cannula 18, thus ensuring that air cannot flow between the blunting member 14 and needle cannula 18 in response to the coupling of an evacuated tube to the opposite end 14b of the blunting member 14, i.e., the end of the blunting member disposed oppositely with respect to the end located within the needle cannula 18. The viscous lubricant also ensures that all fluid directed to such an evacuated tube or the like will flow through the tubular blunting member 14.

As indicated above, internal component 12 is movable relative to external component 10 between an initial or retracted position as shown in FIG. 3, wherein the end of blunting member 14 is disposed within the front needle cannula leaving the puncture tip 18a exposed, and the extended position of FIG. 4 where the blunt first end 14a of blunting member 14 projects beyond the beveled puncture tip 18a, thus shielding puncture tip 18a in the sense that the blunt end prevents puncture tip 18a from effectively contacting tissue to penetrate the same. In a preferred embodiment, the internal component hub 16 and the external component hub 20 are mutually dimensioned and configured to provide an indexing function to set useful mutual positions of the internal component 12 within the external component 10. Two such indexed positions between the (blunting member) internal component 12 and the (needle) external component 10 are defined, in the illustrated embodiment, by annular grooves 30a, 30b provided on the exterior of internal component hub 16 (FIG. 2) and detents 30 of external component hub 20. Groove 30a is seated against detents 30 when the internal component 12 is in its retracted position shown in FIG. 3 and groove 30b is seated against detents 30 when internal component 12 is in its extended position shown in FIG. 4.

FIG. 2A illustrates an alternate embodiment of the invention in which the first guide surface 40 is formed on hub 20, i.e., whereby the first guide member is integral with the hub and part of the assembled device. The other components of FIG. 2A are identical to those of FIGS. 1 and 2, are identically numbered and therefore not further described.

With reference now to FIGS. 5 and 6, a self-blunting needle assembly 15' in accordance with an alternate embodiment of the present invention is shown. It should be appreciated that this alternate embodiment is similar to the embodiment of FIGS. 1–4 in both form and function and, therefore, like reference numerals have been used to refer to like elements, sometimes with a prime indicator. The primary difference between the embodiment of FIGS. 1–4 and the embodiment of FIGS. 5 and 6 is a reversal of the concentric relation between the blunting member and the needle cannula. That is, in the embodiment of FIGS. 5 and 6, the internal component 12' of the device comprises a needle cannula 18' and an internal component hub 16' thereon. The internal component 12' is disposed within an external component 10', i.e., within hollow blunting member 14' thereof. External component 10' further comprises the external component hub 20' within which blunting member 14' is fixedly mounted by means of a ferrule 22' associated therewith.

The self-blunting needle assembly 15' of FIGS. 5 and 6 is assembled in a manner which is substantially similar to that described with respect to the embodiment of FIGS. 1–4. That is, blunting member 14' is mounted in ferrule 22' in the same manner as described above for the mounting of needle cannula 18' into ferrule 22 of the FIGS. 1–4 embodiment, utilizing second guide surface 42'. Needle cannula 18' is then inserted into hub 20 and is guided by first guide surface 40' to the interior bore of blunting member 14'. A lubricant (not shown) is applied to the exterior of needle cannula 18' which is advanced by the use of an actuation member until it projects beyond the blunt first end 14a' of blunting member 14', thus disposing the device in a sharpened configuration by exposing puncture tip 18a'. Upon use of needle assembly 15', needle cannula 18' is withdrawn into a retracted position within blunting member 14' to dispose the device in a blunted configuration. It will be noted that the embodiment of FIGS. 5 and 6 lacks the equivalent of grooves 30a, 30b shown in the embodiment illustrated in FIGS. 2–4. In the embodiment of FIGS. 5 and 6, other means (not shown) may be employed to retain the components in the respective positions illustrated in FIGS. 5 and 6. For example, locking or detent means may be provided on an actuator which engages opposite end 14b' in order to retain internal component 12' in its two positions illustrated in FIGS. 5 and 6. Alternatively, internal component hub 16' of FIGS. 5 and 6 could be configured to have grooves similar or identical to grooves 30a and 30b of the embodiment of FIGS. 2–4.

Naturally, the other component configurations and cooperation discussed above with respect to the first disclosed embodiment apply equally to the embodiment of FIGS. 5 and 6. Further, it should be noted that while needle cannula 18' could assume a variety of tubular configurations, needle 18' is preferably a hollow cannula sharpened at its puncture tip end. Such a configuration allows fluid to be transferred to and/or from a patient through needle 18' in an unobstructed manner.

Figure 7:
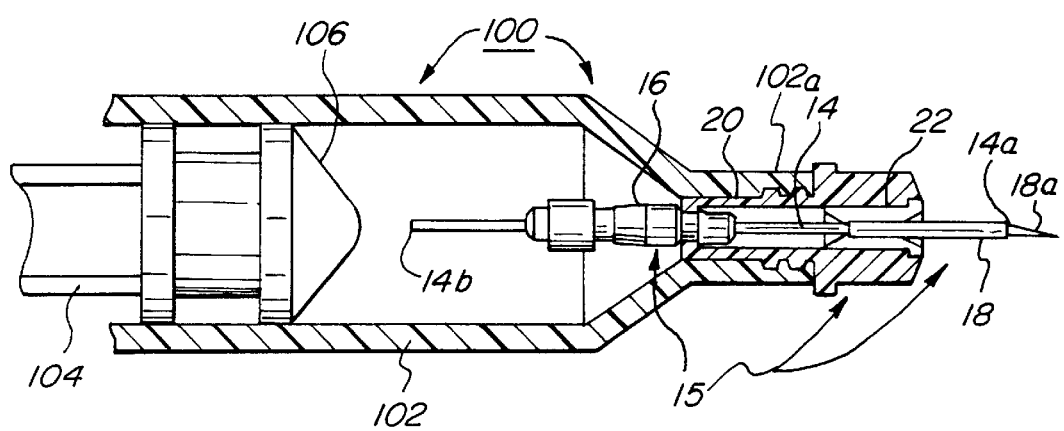
FIG. 7 is a schematic cross-sectional view of a syringe that incorporates a self-blunting needle device in accordance with one embodiment of the invention.

Self-blunting needle assemblies according to the present invention may be employed in a wide variety of venipuncture products such as fluid-collection needles, syringes, catheters, infusion winged sets and various other medical sharps. To give but one particular example, FIG. 7 schematically illustrates a hypodermic syringe 100 that incorporates the self-blunting needle assembly 15 of FIGS. 3 and 4. Syringe 100 comprises a syringe body 102 which is configured to contain a conveniently sized aliquot of injection fluid for hypodermic delivery, e.g., body 102 may comprise a graduated 10 cc cylinder. An actuation member is provided by a plunger 104 on which is mounted a plunger head 106, which slides within body 102 while maintaining a liquid-tight seal therewith. Plunger 104 projects from the end (not shown) of body 102 opposite from needle assembly 15. Body 102 and plunger 104 are configured so that the practitioner can conveniently manipulate syringe 100 by placing his or her fingers on a finger rest (not shown) formed on body 102 and the thumb on a thumb rest (not shown) formed on plunger 104, thus allowing the practitioner to actuate plunger 104 with his or her thumb to force fluid into or out of the syringe body 102 in the conventional manner. Syringe body 102 comprises an internally threaded nose portion 102a that is dimensioned and configured to engage the threads 32 on hub 20 of the self-blunting needle assembly 15. Self-blunting needle assembly 15 is, accordingly, threaded into nose portion 102a of syringe body 102. Prior to using syringe 100, blunting member 14 is in the retracted position, as shown in FIG. 7. After syringe 100 is filled with the injection fluid, needle cannula 18 is inserted through the patient's skin. At this stage, detents 30 engage groove 30a, as shown in FIG. 3. Plunger 104 is then advanced to force the injection fluid through the central bore of blunting member 14 and out from needle cannula 18 into the patient's body. As plunger head 106 moves through the final stage of its stroke for full delivery of the fluid in syringe 100, it bears on self-blunting needle assembly 15, specifically on end 14b thereof, and serves as an actuation member by forcing blunting member 14 to move from the retracted position (shown in FIGS. 3 and 7) to an extended position (shown in FIG. 4) in which the blunt end 14a of blunting member 14 extends beyond the puncture tip 18a of needle cannula 18. The self-blunting needle assembly 15 is retained in the extended position by the function of detents 30 as they fall into groove 30b, as shown in FIG. 4.

FIG. 8A shows another embodiment of a needle cannula and the parts thereof identical or similar to those of the needle cannula illustrated in FIGS. 1–4 are identified by numbers which are 100 higher than those used in the FIGS. 1–4 embodiment. Thus, FIG. 8A shows a needle cannula 118 having a puncture tip 118a and a mounting end 118b. In this embodiment, mounting end 118b has a radially expanded, i.e., outwardly flared, extension 118b' to provide a first guide surface 140 which converges from a first entry aperture 140a to a first gate aperture 140b. In the illustrated embodiment, there is no need for a second guide surface analogous to second guide surface 42 of the FIGS. 1–4 embodiment, because the bore of needle cannula 118 is already coaxially aligned with first gate aperture 140b. In the illustrated embodiment, a mounting ferrule 122 has a circumferential ferrule flange 136 formed thereon for mounting needle cannula 118 in a manner similar or identical to the embodiment of the invention illustrated in FIGS. 1–4. Needle cannula 118 may be efficiently mounted within ferrule 122 by providing ferrule 122 as a split body which is fitted around needle cannula 118, in order to avoid the difficulty (solved by second guide surface 42 in the other illustrated embodiments) of properly coaxially aligning needle cannula 118 with the passage (unnumbered in FIG. 8A, but analogous to passage 38 of FIG. 1A) of mounting ferrule 122'.

Figure 8B:
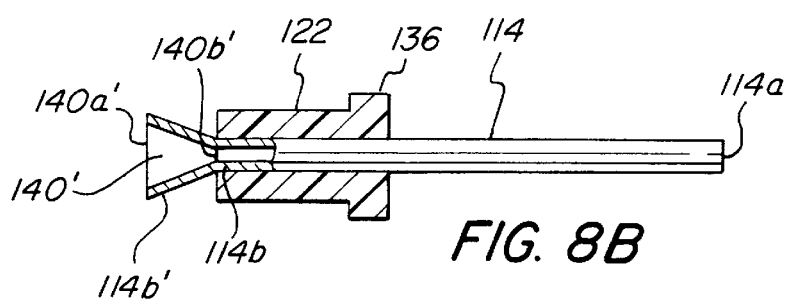
FIG. 8B is a view similar to FIG. 8A of another embodiment of an external component comprising a cannula member utilizable in a needle device similar to that illustrated in FIG. 1.

FIG. 8B shows a blunting member of the type illustrated in FIGS. 5 and 6, wherein the external component is comprised of the blunting member. Accordingly, parts in FIGS. 8B identical or similar to those of FIGS. 5 and 6 are numbered at 100 higher than the corresponding components. Thus, FIG. 8B illustrates a blunting member 114 having a blunt end 114a and whose other end 114b has a radially expanded, i.e., outwardly flared extension 114b' to provide a first entry aperture 140a', a first gate aperture 140b' and a first guide surface 140'. Blunting member 114 is, like needle cannula 118 of FIG. 8A, fitted with a mounting ferrule 122 having a circumferential ferrule flange 136 formed thereon.

Additional embodiments of the present invention are illustrated in FIGS. 8C, 8D, 9A and 9B. The embodiment of FIG. 8C provides a guide surface that leads directly to the through-bore of the external component without converging towards the through-bore. As shown in FIG. 8C, an external component 110 comprising a needle cannula 18 mounted in a hub 120 comprises a guide member such as alignment lug 120a formed integrally therewith. Lug 120a defines a grooved guide surface 60' against which the blunting member 14 of an internal component indicated generally at 12 may be disposed. Guide surface 60' is disposed in parallel relation to the longitudinal axis of needle cannula 18 but is nevertheless positioned and configured to guide blunting member 14 into the through-bore of cannula 18 when the tip of the blunting member is advanced along guide surface 60' towards cannula 18.

In FIG. 8D, still another embodiment of an external component is shown as needle component 110' which is configured generally like needle component 110 of FIG. 8C except that it includes one portion that defines a partially conical guide surface 40" and another portion that defines a grooved guide surface 60" that leads axially to the through-bore of cannula 18. Guide surface 40" and guide surface 60" cooperate in guiding a blunting member into the needle bore in case of misalignment of the internal component and the through-bore. The wide arcuate edge 40a" of guide surface 40" has a configuration that corresponds to a segment of an opening that would be larger than the through-bore of the cannula and thus defines an entry aperture. Guide surface 40" converges axially from the entry aperture at an acute angle relative to the needle axis and then stops converging at a narrow arcuate edge 40b" that similarly defines the gate aperture of the guide surface in a manner analogous to, e.g., gate aperture 40b of guide surface 40 of FIG. 1A.

Referring now to the embodiment of FIG. 9A, two further assembly processes in accordance with the present invention will be described. In the first process, a needle cannula is inserted into a hub to produce a needle component and in the second process a blunting member is inserted into the needle cannula to produce a self-blunting needle cannula device. The first process will illustrate a method of the present invention that makes use of a single guide member and the second process will illustrate an alternative embodiment which makes use of two guide members. For the mounting of a needle cannula 18 in hub 20, the hub is viewed as the external component and the needle cannula as the internal component. The needle and hub are engaged by respective conventional piece handling devices into approximate position for assembly. One handling device brings the external component, i.e., the hub, to a precisely predetermined position. A guide member 50 in the form of a pillow block is provided. Guide member 50 defines a guide surface 58 having a grooved configuration which, in the illustrated embodiment, defines an upwardly-disposed V-shaped groove.

Optionally, guide member 50 may be placed on a flat surface relative to which hub 20 is fixed in position. The piece handling device that engages needle cannula 18 is adapted to permit at least the mounting end 18b of the needle cannula to settle into guide surface 58, either under force of gravity or by mechanical means. Optionally, the needle cannula makes longitudinal contact with the groove as shown in FIG. 9A. Guide member 50 and guide surface 58 therein are positioned in fixed relation to the reference member and are configured so that when needle cannula 18 rests in the groove, the needle cannula 18 is aligned with the internal bore of hub 20 which, in the illustrated embodiment, comprises the passage 38 formed within the ferrule 22. The needle cannula can then be advanced by any conventional means, e.g., by a mechanical ram, by use of pressurized air, movement of guide member 50 as suggested by arrow 54, etc., into the through-bore as seen in the Figure. The internal bore of ferrule 22 defines a shoulder 39 against which the insertion end 18b of needle cannula 18 will come to rest when the needle is fully inserted therein. The hub defines an aperture 40c that opens to passage 38 and to the interior through-bore of the needle cannula. Preferably, the outside of mounting end 18b of needle cannula 18 is treated with adhesive to secure the needle in the hub once it is in place therein. It will be understood that this procedure can be used as well to insert an internal component into a bore that does not extend through the external component.

After the needle is mounted in the hub, the needle hub assembly is treated as an external component into which the blunting member is inserted in a second process according to the present invention. Guide member 50 could be used to provide a guide surface for the insertion of the blunting member into the needle cannula but this would require precisely removing and repositioning the needle member relative to guide member 50. Instead, an alternative embodiment of the invention will be described that makes use of two guide members and that will be applicable for use with needle components (or other external cannula components) that may be previously assembled in any conventional fashion. In accordance with this alternative embodiment, the needle component is disposed with needle cannula 18 in guide surface 58 of guide member 50 by any suitable means. A second guide member 52 is provided which defines a groove 60 in which blunting member 14 may be disposed by any suitable means. Guide member 52 is dimensioned and configured so that when blunting member 14 rests in groove 60 and needle cannula 18 is in guide surface 58, the mounting end of the blunting member is aligned with the through-bore of needle cannula 18. Then, the blunting member is advanced into the needle cannula, e.g., by moving guide member 52 as suggested by arrow 56 or by any other suitable means. The blunting member passes into and through the needle component until it extends from the needle hub 20 to permit the mounting of an internal component hub or "nut" 16 (e.g., FIG. 2A) thereon. The resulting concentrically disposed blunting component and needle component can then be removed from the guide member(s) and secured to a syringe or other device in a conventional manner. The guide member(s) can then be re-used to facilitate the assembly of another device.

As described with reference to FIG. 9A, the mounting end of the blunting member was inserted into the insertion tip of the needle cannula. However, in an alternative embodiment of the invention, a guide member configured to provide a guide surface that leads axially to hub aperture 40c could be disposed at the opposite end of the needle component so that the tip of blunting member 14 is aligned with, and is inserted into, the mounting end 18b of needle cannula 18 through hub 20 via aperture 40c. In such case, the blunting member hub may optionally be mounted on the blunting member before the blunting member is inserted into the needle cannula.

It will be understood that the V-shaped configuration of grooves 58 and 60 are illustrative only and any suitable groove geometry which functions to align the needle cannula 18 and blunting member 14 for assembly thereof may also be employed in the practice of this aspect of the invention. For example, the apex of guide surface 58 need not be angular in cross section as illustrated, but could be curvilinear in cross section. It will also be understood that the concentric relation between the blunting member and the needle cannula may be reversed (not shown), as discussed above in connection with FIGS. 5 and 6.

In an alternative embodiment, a guide member may be configured to define two guide surfaces comprising grooves of differing configurations. For example, a guide member 52', FIG. 9B, resembling the end-to-end joinder of guide members 50 and 52 could be formed and would thus define a guide surface that comprises two grooves 58 and 60 on the same structure. The resulting guide member 52' would thus permit the positioning of the needle cannula in guide surface 58 and the positioning of a blunting member in the groove 60 to facilitate insertion of the blunting member into the needle by moving the blunting member into the needle cannula, as suggested by arrow 56'.

Figure 10:
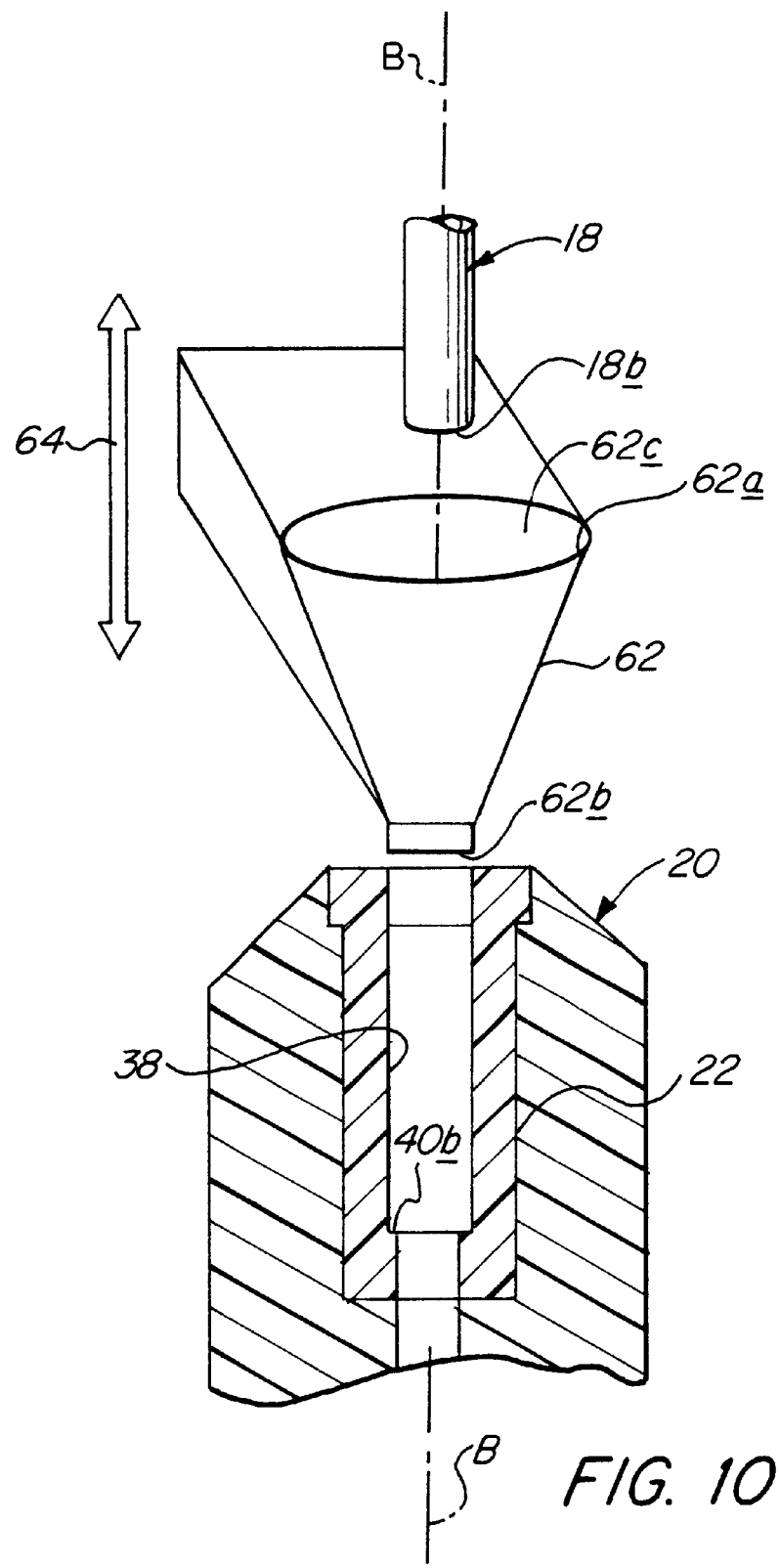
FIG. 10 is a schematic elevation view illustrating a step of a method aspect of the present invention.

Referring now to FIG. 10, in this embodiment a vertical assembly process is contemplated wherein the guide member comprises a funnel 62 which may, e.g., reciprocate in the direction of arrow 64 as described hereafter. As illustrated, the internal component, i.e., needle cannula 18, funnel 62, and external hub 20 are disposed in spaced relationship along a vertical axis B. The funnel is employed to facilitate insertion of an internal component, in this case needle cannula 18, into an external component, in this case hub 20, having a passage 38 which provides a through-bore therein. Funnel 62 defines an entry aperture 62a and an exit aperture 62b. The internal diameter of exit aperture 62b is not larger than the entrance of passage 38 into which the internal component is to be inserted, and the entry aperture 62a is larger than the exit aperture. Funnel 62 comprises an internal guide surface 62c that converges axially from the entry aperture 62a to the exit aperture 62b. In operation, funnel 62 is positioned with exit aperture 62b aligned with passage 38. The mounting end 18b of the internal component is aligned with entry aperture 62a and is advanced into the funnel. This may be achieved in a vertical assembly process by positioning the funnel vertically over the external component, positioning the internal component above the entry aperture of the funnel, and releasing the internal component so that it is pulled by gravity into the funnel. The needle will come to rest on internal shoulder 39. A second funnel having an exit aperture not larger than the through-bore of the needle may be used in a similar manner to facilitate the insertion of the blunting member into the needle. The blunting member will be configured to pass through the needle and through the hub so that the blunting member hub or "nut" can be secured to the bottom end of the blunting member.

Figure 11A:
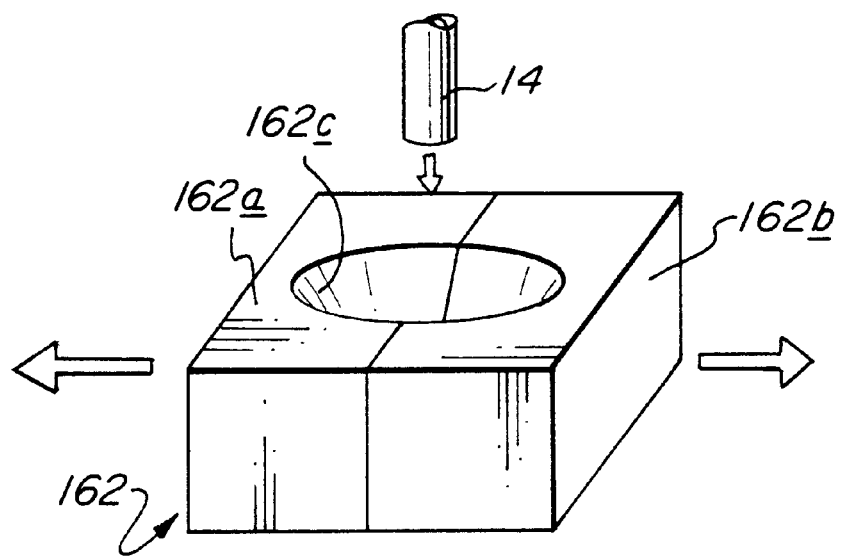
FIG. 11A is a schematic perspective view of a split guide member in accordance with the present invention, shown with two halves together in a working configuration.
Figure 11B:
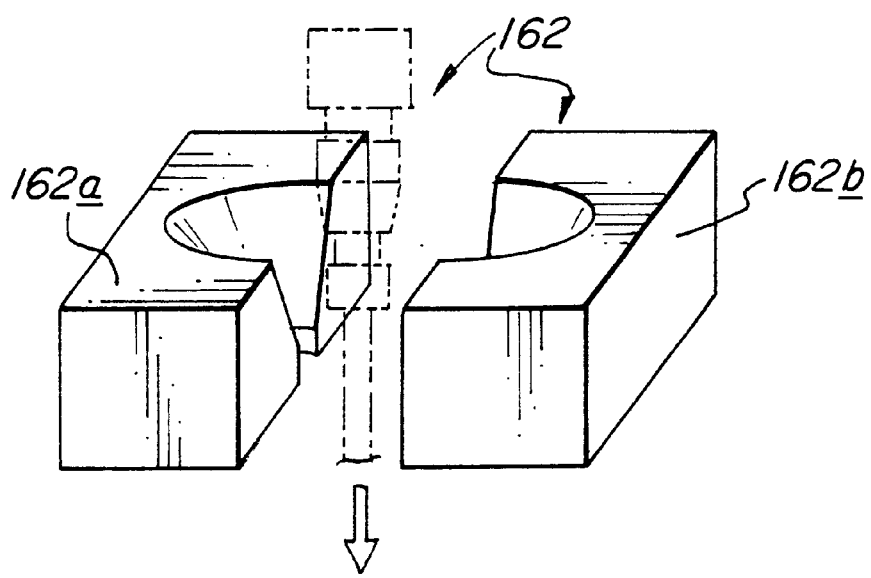
FIG. 11B shows the guide member of FIG. 11A with the two halves in a separated configuration.

Alternatively, the needle component, i.e., the hub 20 with the needle 18 secured therein, may be inverted and the blunting member may be introduced into the mounting end of the needle through-bore. In such case, the guide member may be embodied as a split fixture having separable halves that are movable between a working configuration illustrated schematically in FIG. 11A and a separated configuration illustrated schematically in FIG. 11B. In the working configuration, an assembly fixture holds parts 162a and 162b together so that they cooperate to form a generally conical, funnel-like guide surface 162c, as shown in FIG. 11A. The fixture 162 is positioned so that the exit aperture of the guide surface (not visible in FIG. 11A) is aligned with the mounting end of a needle cannula. The tip of a blunting member 14 is then aligned with the guide surface 162c, e.g., by directing it downward from above, and is brought in contact therewith and is advanced therethrough so that it is guided to the exit aperture and then into the needle cannula. The nut on the blunting member (shown in dotted outline in FIG. 11B) is larger than the exit aperture of the guide surface 162c and cannot pass therethrough, so after the blunting member has entered the needle cannula, parts 162a and 162b are separated as suggested by the unnumbered arrows in FIG. 11A. The fixture 162 thus attains the separated configuration of FIG. 11B. The self-blunting needle device may thus be assembled and removed from the fixture 162. The fixture 162 can then be moved back to the working configuration of FIG. 11A and positioned for use in inserting another blunting member into another needle cannula.

In the embodiments of FIGS. 9A, 9B and 10, the guide member is not an integral part of the finished self-blunting needle device, so the method for the assembly of the needle device may comprise removing the assembled device from the guide member.

In the embodiments of FIGS. 1–4, the needle cannula 18 in the hub 20 may be considered the reference member because its position is fixed relative to the first guide surface (e.g., surface 40, FIG. 2A) which guides the misaligned complementary member, i.e., the blunting member 14, into the cannula through-bore.

In the embodiments of FIGS. 5 and 6, the blunting member 14' is the reference member because it is fixed in position relative to the guide surface 40' and the needle cannula 18' constitutes the complementary member.

While several preferred embodiments have been shown and described, various modifications and substitutions may be made thereto without departing from the spirit and scope of the invention. Accordingly, it is to be understood that the present invention has been described by way of illustration and not limitation.

What is claimed is:

1. A self-blunting needle cannula device comprising:
   (a) an external component comprising a needle cannula having a through-bore, a tip comprising a puncture tip, a mounting end, and an external component hub on the needle cannula spaced from the tip;
   (b) an internal component comprising an elongate blunting member having a tip defining a blunt tip, and an internal component hub on the blunting member being disposed within the through-bore of the needle cannula;
   (c) wherein the external component and the internal component are movable relative to each other between a sharpened configuration in which the blunt tip is positioned short of the puncture tip of the needle cannula to leave the puncture tip exposed, and a blunting configuration in which the blunt tip extends beyond the puncture tip of the needle cannula to effectively blunt the device;

(d) a guide surface on the device that leads axially towards the through-bore so that the guide surface can serve as a guide for the insertion of the blunting member into the through-bore during assembly of the device; and a detent and groove engagement between the external component and the internal component configured to inhibit movement from the blunting configuration to the sharpened configuration.

2. The device of claim 1 wherein the guide surface converges axially from a first entry aperture larger than the through-bore to a first gate aperture not larger than the through-bore, the first gate aperture being aligned with the through-bore.

3. The device of claim 1 wherein the guide surface comprises a non-convergent surface that defines a groove that is positioned and configured to guide the blunting member into the through-bore of the needle cannula.

4. The device of claim 3 wherein the guide surface further comprises a portion that converges axially from a first entry aperture larger than the through-bore to a first gate aperture not larger than the through-bore, the first gate aperture being aligned with the through-bore.

5. The device of claim 3 or claim 4 wherein the first entry aperture has a diameter in the range of from about 0.5 to 0.009 inch and the first gate aperture has a diameter in the range of from about 0.203 to 0.006 inch.

6. The device of claim 2 wherein the needle cannula defines a longitudinal axis and wherein at least a portion of the guide surface defines an angle α relative to the needle cannula axis and wherein the angle has a magnitude in the range of from about 5 to 75 degrees.

7. The device of claim 2 or claim 3 comprising a guide member disposed at the mounting end of the needle cannula, the guide member defining the guide surface.

8. The device of claim 7 wherein the guide member is disposed within the external component hub.

9. The device of claim 7 wherein the guide member is integrally formed as part of the external component hub.

10. The device of claim 9 wherein the guide member comprises an alignment lug formed on the external component hub.

11. The device of claim 3 comprising a guide member having a first end at which the first guide surface is formed and an opposite, second end at which is formed a second entry aperture larger than the needle cannula and a second guide surface that converges axially to a second gate aperture smaller than the second entry aperture but not smaller than the needle cannula, the guide member further comprising a passage extending between and axially aligned with the first and second gate apertures, the needle cannula extending through the second gate aperture and the mounting end of the needle cannula being mounted within the passage, and wherein the second guide surface converges from the second entry aperture towards the bore to the second gate aperture, to serve as a guide for the insertion of the mounting end of the needle cannula into the passage during assembly of the device.

12. The device of claim 11 wherein the first gate aperture is smaller than the passage in the guide member and smaller than the needle cannula so that the guide member defines in the passage a stop shoulder at the first gate aperture.

13. The device of claim 11 wherein the second entry aperture has a diameter in the range of from about 0.5 to 0.009 inch and the second gate aperture has a diameter in the range of from about 0.203 to 0.006 inch.

14. The device of claim 11 wherein the second guide surface defines an angle α relative to the needle cannula axis and wherein the angle has a magnitude in the range of from about 5 to 75 degrees.

15. The device of any one of claims 1–4 in combination with a syringe comprising an actuation member for moving the device from a sharpened configuration to a blunted configuration.

16. The device of claim 1 wherein the detent and groove engagement is dimensioned and configured to releasably maintain the device in the sharpened configuration prior to its movement to the blunted configuration.

17. A method for assembling a self-blunting needle device for a syringe, the device comprising an internal component comprising a blunting member and an external component comprising a needle cannula having an axially-extending through-bore therein, the method comprising advancing the blunting member into contact with a guide surface configured to lead axially to the through-bore to guide the blunting member into the bore and advancing the blunting member along said guide surface and into the through-bore without engaging a catch surface perpendicular to the needle cannula, to produce an assembled device.

18. The method of claim 17 comprising advancing the internal component into contact with a non-convergent guide surface.

19. The method of claim 17 comprising advancing the internal component into contact with an axially convergent guide surface.

20. The method of claim 19 wherein the guide surface defines an entry aperture that is larger than the through-bore of the external component and converges to a gate aperture that is not larger than the through-bore of the external component, the gate aperture facing and being aligned with the through-bore, the method comprising aligning the internal component with the entry aperture and advancing the internal component towards the external component so that the internal component passes through the entry aperture, into contact with the guide surface and then through the aperture and into the bore.

21. The method of claim 17, claim 18 or claim 19 comprising contacting the external component with a first guide surface and contacting the internal component with a second guide surface.

22. The method of claims 17, 18, 19 or 20 wherein the guide surface is provided by a non-integral guide member and wherein the method comprises removing the assembled device from the guide member.

23. The method of claim 22 wherein the external component comprises a cannula having a tip and a mounting end mounted in a hub, the hub defining an aperture that permits access to the through-bore by the internal component, wherein the guide member comprises a funnel having a gate aperture and an exit aperture and wherein the method comprises aligning the gate aperture of the funnel with the through-bore at the tip of the cannula, passing the internal component through the guide member and removing the assembled device from the guide member.

24. The method of claim 23 further comprising securing a nut to the internal component after the internal component passes through the guide member.

25. The method of claim 17 further comprising mounting the self-blunting needle device on a syringe.

26. A method for assembling a self-blunting needle device comprised of (i) an external component comprising a needle cannula having a through-bore, a puncture tip and a mounting end and a guide member having a first end and a second end and a passage that extends axially from the first end to the second end and further comprising at the first end a first guide surface that leads axially to the passage and at the second end a second guide surface that leads axially to the passage, wherein the passage is sized to receive the needle cannula; and (ii) an internal component comprising an elongate blunting member having a blunt tip, and, after assembly, being disposed within the through-bore of the needle cannula;

the method comprising the steps of:

(a) disposing the needle cannula with its mounting end disposed towards and in alignment with the second guide surface and advancing the needle cannula into contact with the second guide surface and into the passage and into alignment with the first gate aperture, (b) positioning a guide member having a guide surface relative to the external component so that the guide surface leads axially to the through-bore; and (c) advancing the blunting member into contact with the guide surface to guide the blunting member into the through-bore of the needle cannula.

27. The method of claim 26 comprising providing a guide member having a first end and a second end and a passage that extends axially from the first end to the second end and further comprising at the first end a first guide surface that leads axially to a first gate aperture aligned with the passage and at the second end a second guide surface that leads axially to the passage, wherein the passage is sized to receive the needle cannula, the method further comprising, before steps (a) and (b), disposing the needle cannula with its mounting end disposed towards and in alignment with the second guide surface and advancing the needle cannula into contact with the second guide surface and into the passage and into alignment with the first gate aperture.

28. The method of claim 26 further comprising the steps of installing the self-blunting needle device in a medical fluid-handling device comprising an actuation member for moving the device between the sharpened configuration and the blunted configuration.

* * * * *